United States Patent [19]

Kinoshita et al.

[11] Patent Number: 5,614,527
[45] Date of Patent: Mar. 25, 1997

[54] INSECTICIDAL TETRAHYDROFURAN-COMPOUND

[75] Inventors: Katsutoshi Kinoshita; Takeo Wakita; Kenji Kodaka; Hirozumi Matsuno; Kenichi Satoh; Shirou Shiraishi; Kazutomi Ohnuma; Eiichi Yamada; Naoko Yasui; Nobuyuki Kawahara; Koichi Ebihara; Michihiko Nakaya, all of Chiba-ken, Japan

[73] Assignee: Mitsui Toatsu Chemicals, Inc., Tokyo, Japan

[21] Appl. No.: 447,962

[22] Filed: May 23, 1995

[30] Foreign Application Priority Data

Jun. 3, 1994 [JP] Japan .................................. 6-122179
Mar. 23, 1995 [JP] Japan .................................. 7-064120

[51] Int. Cl.$^6$ .................. C07D 251/08; A01N 43/54
[52] U.S. Cl. .................................. 514/256; 544/332
[58] Field of Search ................. 544/332; 514/256, 514/275

[56] References Cited

FOREIGN PATENT DOCUMENTS

| 0192060 | 8/1986 | European Pat. Off. . |
| 0277317 | 8/1988 | European Pat. Off. . |
| 61-183271 | 8/1986 | Japan . |
| 61-267575 | 11/1986 | Japan . |
| 62-81382 | 4/1987 | Japan . |
| 63-156786 | 6/1988 | Japan . |
| 4-120054 | 4/1992 | Japan . |
| 5-9173 | 1/1993 | Japan . |

OTHER PUBLICATIONS

*The Journal of the American Chemical Society,* "levo-2, 3-Dinitroxybutane", A. F. McKay et al, vol. 70, pp. 430–431, 1948. (Abstract).
*Journal of Pesticide Science,* "Development of a Chloronicotinyl Insecticide, Imidacloprid", Kozo Shiokawa et al, pp. 329–332, 1994 (Abstract).
*Journal of Pesticide Science,* "Development of a Chloronicotinyl Insecticide, Imidacloprid", Kozo Shiokawa et al, pp. 209–217, (1994). (No Abstract).

*Primary Examiner*—John M. Ford
*Attorney, Agent, or Firm*—Burns, Doane, Swecker & Mathis

[57] ABSTRACT

A tetrahydrofuran-compound is disclosed herein which is represented by the formula (1)

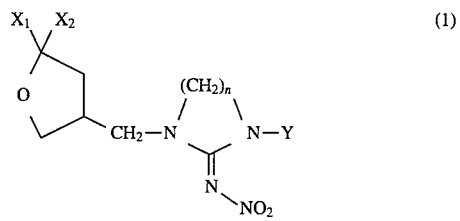

wherein each of $X_1$ and $X_2$ is a hydrogen atom or a methyl group, Y is a hydrogen atom or a carbonyl group substituted by a lower alkyl group (Y') having 1 to 4 carbon atoms, i.e., an acyl group (—COY'), and n is 2 or 3, and an insecticide containing the tetrahydrofuran-compound as an effective component.

8 Claims, No Drawings

INSECTICIDAL TETRAHYDROFURAN-COMPOUND

BACKGROUND OF THE INVENTION

1. Field of the Invention

The present invention relates to a tetrahydrofuran-compound and a novel insecticide containing this compound as an effective component.

The tetrahydrofuran-compound of the present invention is useful as a pesticide (particularly an insecticide) in the agricultural field.

2. Description of the Prior Art

An insecticidal tetrahydrofuran-compound of the present invention can be represented by the formula (1) which will be described hereinafter, but another insecticidal compound having a similar skeleton has been described in Japanese Patent Application Laid-open No. 183271/1986. However, the disclosed compound is a nitromethylene-compound, which is different in structure from the compound of the present invention having a nitroimino group. On the other hand, Japanese Patent Application Laid-open No. 81382/1987 has the description of an insecticide having a skeleton similar to that of the compound of the present invention. In this publication, a compound having a furan ring which is a kind of unsaturated ring as a part of the skeleton is mentioned, but there is not described any compound having a tetrahydrofuran ring which is a kind of saturated ring as a part of the skeleton such as the compound of the present invention. Furthermore, Japanese Patent Application Laid-open No. 156786/1988 has reported a compound having a skeleton similar to that of the compound of the present invention as an intermediate of an insecticide, but in this publication, the insecticidal activity of this intermediate has not been referred to anywhere. Therefore, in the former techniques, there has been found neither the description of compounds having such a structure as in the present invention nor the description of a use as insecticides of these compounds.

Moreover, the above-mentioned patent publications have a description that the compound containing a heterocyclic group in its molecule shows insecticidal activity. However, according to investigations by the present inventors, it has been elucidated that every heterocyclic ring does not show the insecticidal activity. That is to say, among these insecticidal compounds, the compounds having the practical activity as a pesticide are limited to derivatives having a thiazolylmethyl group or a pyridylmethyl group as a part of the skeleton, and this fact has also been reported in an industrial magazine [J. Pesticide Sci., 19, S209 (1994)] and the like. Furthermore, imidacloprid is the only compound which has the pyridylmethyl group as a part of the skeleton, and has now been put to practical use. That is to say, according to the former techniques, although it has been suggested that all compounds containing a heterocyclic group in the molecule shows insecticidal activity, the heterocyclic groups having insecticidal activity are limited. In addition, the practically useful compounds are limited to the derivatives having the pyridylmethyl group as a part of the skeleton.

SUMMARY OF THE INVENTION

Therefore, an object of the present invention is to provide a novel nitroimino-compound having neither a pyridylmethyl group nor a thiazolylmethyl group in its molecule, exhibiting an excellent insecticidal activity, and having a low toxicity to mammals which is required as a pesticide.

The present inventors have intensively investigated to solve the above-mentioned problem, and as a result, it has been found that a tetrahydrofuran-compound represented by the formula (1) has an excellent insecticidal activity in spite of no pyridylmethyl group in a molecular structure and is less toxic. In consequence, the present invention has been completed.

That is to say, the present invention is directed to a tetrahydrofuran-compound represented by the formula (1)

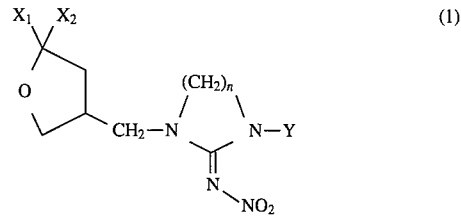

wherein each of $X_1$ and $X_2$ is a hydrogen atom or a methyl group, Y is a hydrogen atom or a carbonyl group substituted by a lower alkyl group (Y') having 1 to 4 carbon atoms, i.e., an acyl group(—COY'), and n is 2 or 3, and an insecticide containing the tetrahydrofuran-compound as an effective component.

The tetrahydrofuran-compound represented by the formula (1) of the present invention is an excellent compound having a high insecticidal activity and a wide insecticidal spectrum and having an extremely low toxicity to mammals. In addition, the pesticide containing the tetrahydrofuran-compound represented by the formula (1) of the present invention has excellent characteristics and is useful as an insecticide.

DETAILED DESCRIPTION OF THE INVENTION

Typical examples of an acyl group having 2 to 5 carbon atoms which is represented by Y in the above-mentioned formula (1) include a methylcarbonyl group, an ethylcarbonyl group, a n-propylcarbonyl group, an isopropylcarbonyl group and a tert-butylcarbonyl group and so on, and preferable are the methylcarbonyl group and the iso-propylcarbonyl group. The compound of the formula (1) can be prepared by the use of any of a method A, a method B and a method C which will be described hereinafter.

Method A

A compound represented by the formula (1) in which $X_1$, $X_2$, Y and n are as defined above can be prepared in accordance with the following reaction formula (I):

Reaction formula (I)

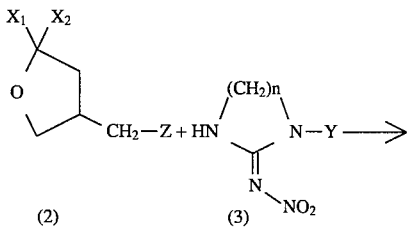

3
-continued
Reaction formula (I)

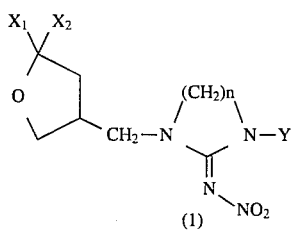

wherein $X_1$, $X_2$, Y and n are as defined above, and Z is a halogen atom, a toluenesulfonyloxy group, a methanesulfonyloxy group or a trifluoromethanesulfonyloxy group.

That is to say, the compound represented by the formula (1) can be easily prepared in a high yield by reacting the compound represented by the formula (2) with the compound represented by the formula (3) in the presence of a base.

The reaction can be carried out, if necessary, in the presence of the base in a kind of solvent to permit the easy preparation.

Examples of the base include alkali metal hydroxides such as sodium hydroxide and potassium hydroxide, alkaline earth metal hydroxides such as magnesium hydroxide and calcium hydroxide, alkali metal hydrides such as sodium hydride and potassium hydride, alkali metal alcoholates such as sodium methylate and sodium ethylate, alkali metal oxides such as sodium oxide, carbonates such as potassium carbonate and sodium carbonate, phosphates such as tripotassium phosphate, trisodium phosphate, dipotassium hydrogenphosphate and disodium hydrogenphosphate, acetates such as sodium acetate and potassium acetate, and organic bases such as 4-(dimethylamino)pyridine, DABCO, triethylamine and diazabicycloundecene.

Examples of the solvent include water, alcohols such as methanol, ethanol, propanol and butanol, aromatic hydrocarbons such as benzene, toluene and xylene, aliphatic hydrocarbons such as hexane, heptane and petroleum benzin, aprotic polar solvents such as dimethylformamide, dimethylacetamide, dimethyl sulfoxide, 1,3-dimethyl-2-imidazolidinone and 1-methyl-2-pyrrolidinone, ethers such as ethyl ether, diisopropyl ether, 1,2-dimethoxyethane, tetrahydrofuran and dioxane, nitriles such as acetonitrile and propionitrile, and ketones such as acetone and diisopropyl ketone.

A reaction temperature and a reaction time are changeable in wide ranges, but in general, the reaction temperature is in the range of −30° to 200° C., preferably room temperature to 150° C. and the reaction time is in the range of 0.01 to 50 hours, preferably 0.1 to 15 hours.

The compound represented by the formula (2) in the above-mentioned reaction formula (I) can be prepared by halogenating (tetrahydro-3-furanyl)methanol with a halogenating agent such as thionyl chloride, phosphorus oxychloride, phosphorus tribromide, triphenylphosphine/carbon tetrabromide or triphenylphosphine/carbon tetrachloride, or alternatively by sulfonating (tetrahydro-3-furanyl)methanol with a sulfonating agent such as tosyl chloride, methanesulfonyl chloride and trifluoromethanesulfonic anhydride.

The compound represented by the formula (3) in the reaction formula (I) is a known compound, and it can be prepared in accordance with a procedure described in J. Am. Chem. Soc., Vol. 70, p. 430 (1948) and the like.

4
Method B

A compound represented by the formula (1A), which is a compound of the formula (1) in which $X_1$, $X_2$ and n are as defined above and Y is a hydrogen atom, can be prepared in accordance with the following reaction formula (II):

Reaction formula (II)

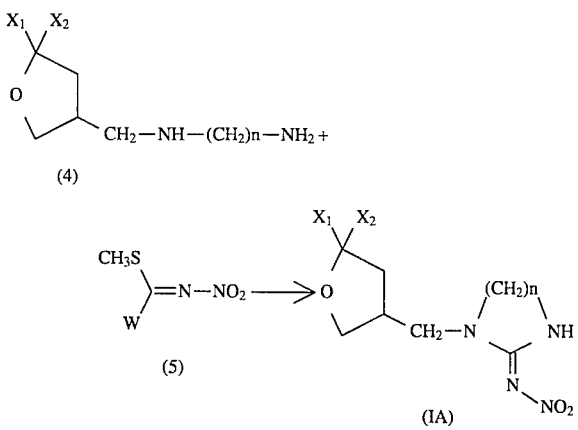

wherein $X_1$, $X_2$ and n are as defined above, and W is an amino group, a methylthio group or a phthalimide group.

That is to say, the compound represented by the formula (1A) can easily be prepared in a high yield by reacting the compound represented by the formula (4) with the compound represented by the formula (5) in a molar ratio of 10:1 to 1:10, preferably 1:2 to 2:1.

The reaction can be carried out, if necessary, in the presence of a base or a catalyst in a kind of solvent to permit the easy preparation.

Examples of the base which can be used in the above-mentioned reaction include carbonates such as potassium carbonate and sodium carbonate, phosphates such as tripotassium phosphate, trisodium phosphate, dipotassium hydrogenphosphate and disodium hydrogenphosphate, and acetates such as sodium acetate and potassium acetate.

Furthermore, examples of the catalyst include organic bases such as 4-(dimethylamino)pyridine, DABCO, triethylamine and diazabicycloundecene, sulfonic acids such as p-toluenesulfonic acid and methanesulfonic acid, mineral acids such as sulfuric acid, hydrochloric acid and phosphoric acid, ion exchange resins, silica gels and zeolites.

Examples of the solvent which can be used in the reaction include water, alcohols such as methanol, ethanol, propanol and butanol, aromatic hydrocarbons such as benzene, toluene and xylene, aliphatic hydrocarbons such as hexane, heptane and petroleum benzin, aprotic polar solvents such as dimethylformamide, dimethylacetamide, dimethyl sulfoxide, 1,3-dimethyl-2-imidazolidinone and 1-methyl-2-pyrrolidinone, ethers such as ethyl ether, diisopropyl ether, 1,2-dimethoxyethane, tetrahydrofuran and dioxane, nitriles such as acetonitrile and propionitrile, and ketones such as acetone and diisopropyl ketone.

A reaction temperature and a reaction time are changeable in wide ranges, but in general, the reaction temperature is in the range of −20° to 200° C., preferably 0° to 150° C. and the reaction time is in the range of 0.01 to 50 hours, preferably 0.1 to 15 hours.

The compound represented by the formula (4) in the above-mentioned reaction formula (II) can be prepared in accordance with the following reaction formula (IIa):

Reaction formula (IIa)

$$\underset{(2)}{\overset{X_1\phantom{xx}X_2}{\diagdown\phantom{x}\diagup}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!}{O}}$$

(structure 2): X₁X₂C(O-)(CH₂-Z) — epoxide with CH₂—Z + H₂N—(CH₂)n—NH₂ (6) →

(structure 4): X₁X₂C(O-)(CH₂—NH—(CH₂)n—NH₂) — epoxide wherein $X_1$, $X_2$ and n are as defined above, and Z is a halogen atom, a toluenesulfonyloxy group, a methanesulfonyloxy group or a trifluoromethanesulfonyloxy group.

That is to say, the compound represented by the formula (4) can easily be prepared in a high yield by reacting the compound represented by the formula (2) with a compound represented by the formula (6) in a molar ratio of 10:1 to 1:10, preferably 1:2 to 2:1.

In the reaction, as the base, the compound of the formula (6) may be used in an excess amount, or alternatively, if, necessary, other bases may be added and the reaction is carried out in no solvent or a kind of solvent to permit the easy preparation. Examples of the base include alkali metal hydroxides such as sodium hydroxide and potassium hydroxide, alkaline earth metal hydroxides such as magnesium hydroxide and calcium hydroxide, alkali metal hydrides such as sodium hydride and potassium hydride, alkali metal alcoholates such as sodium methylate and sodium ethylate, an alkali metal oxide such as sodium oxide, carbonates such as potassium carbonate and sodium carbonate, phosphates such as tripotassium phosphate, trisodium phosphate, dipotassium hydrogenphosphate and disodium hydrogenphosphate, acetates such as sodium acetate and potassium acetate, and organic bases such as 4-(dimethylamino)pyridine, DABCO, triethylamine and diazabicycloundecene.

Examples of the solvent include water, alcohols such as methanol, ethanol, propanol and butanol, aromatic hydrocarbons such as benzene, toluene and xylene, aliphatic hydrocarbons such as hexane, heptane and petroleum benzin, aprotic polar solvents such as dimethylformamide, dimethylacetamide, dimethyl sulfoxide, 1,3-dimethyl-2-imidazolidinone and 1-methyl-2-pyrrolidinone, ethers such as ethyl ether, diisopropyl ether, 1,2-dimethoxyethane, tetrahydrofuran and dioxane, nitriles such as acetonitrile and propionitrile, and ketones such as acetone and diisopropyl ketone.

A reaction temperature and a reaction time are changeable in wide ranges, but in general, the reaction temperature is in the range of −30° to 200° C., preferably −20° to 150° C. and the reaction time is in the range of 0.01 to 50 hours, preferably 0.1 to 15 hours.

The compound represented by the formula (2) in the above-mentioned reaction formula (IIa) can be prepared in the above-mentioned manner.

The compound represented by the formula (6) in the reaction formula (IIa) is a known compound. The compound represented by the formula (5) in the reaction formula (II) can be prepared in accordance with methods described in Japanese Patent Application Laid-open Nos. 120054/1992 and 9173/1993 and the like.

Method C A compound represented by the formula (1B), which is a compound of the formula (1) in which $X_1$, $X_2$ and n are as defined above and Y is a carbonyl group substituted by a lower alkyl group (Y') having 1 to 4 carbon atoms, i.e., an acyl group (—COY'), can be prepared in accordance with the following reaction formula (III):

Reaction formula (III)

(1A): epoxide with CH₂—N<(CH₂)n>C(=N—NO₂)—NH + Y'—C(=O)—Cl (7) →

(1B): epoxide with CH₂—N<(CH₂)n>C(=N—NO₂)—N—C(=O)—Y'

That is to say, the compound represented by the formula (1B) can easily be prepared in a high yield by reacting the compound represented by the formula (1A) with a compound represented by the formula (7).

The reaction can be carried out in the presence of a base in a kind of solvent to permit the easy preparation, Examples of the base include alkali metal hydroxides. such as sodium hydroxide and potassium hydroxide, alkaline earth metal hydroxides such as magnesium hydroxide and calcium hydroxide, alkali metal hydrides such as sodium hydride and potassium hydride, alkali metal alcoholates such as sodium methylate and sodium ethylate, alkali metal oxides such as sodium oxide, carbonates such as potassium carbonate and sodium carbonate, phosphates such as tripotassium phosphate, trisodium phosphate, dipotassium hydrogenphosphate and disodium hydrogenphosphate, acetates such as sodium acetate and potassium acetate, and organic bases such as pyridine, 4-(dimethylamino)pyridine, DABCO, triethylamine and diazabicycloundecene.

Examples of the solvent include water, alcohols such as methanol, ethanol, propanol and butanol, aromatic hydrocarbons such as benzene, toluene and xylene, aliphatic hydrocarbons such as hexane, heptane and petroleum benzin, aprotic polar solvents such as dimethylformamide, dimethylacetamide, dimethyl sulfoxide, 1,3-dimethyl-2-imidazolidinone and 1-methyl-2-pyrrolidinone, ethers such as ethyl ether, diisopropyl ether, 1,2-dimethoxyethane, tetrahydrofuran and dioxane, nitriles such as acetonitrile and propionitrile, ketones such as acetone and diisopropyl ketone, and chlorine-containing solvents such as methylene chloride and chloroform.

A reaction temperature and a reaction time are changeable in wide ranges, but in general, the reaction temperature is in the range of −20° to 200° C., preferably 0° to 150° C. and the reaction time is in the range of 0.01 to 50 hours, preferably 0.1 to 15 hours.

The compound represented by the formula (1A) in the reaction formula (III) can be prepared by the methods of the reaction formulae (I) and (II).

The compound represented by the formula (7) in the reaction formula (III) can be prepared from a known carboxylic acid in accordance with the synthetic method of a known carbonyl chloride.

The compound represented by the formula (1) may be present in the state of isomers (a cis-isomer and a trans-isomer) or a tautomer. Furthermore, an asymmetric carbon may be present at the 3-position of a tetrahydrofuran ring, and so the compound may be present in the form of the optical isomers, the racemic form, or a mixture of them in an optional ratio.

When the tetrahydrofuran ring is substituted by alkyl groups, diastereomers sometimes exist, and these isomers can be present as a mixture of them in an optional ratio. All the isomers, the tautomer and the mixture of these isomers are included in the present invention.

Heretofore, the insecticidal compounds having a nitromethylene group, a nitroimino group or a cyanoimino group have been disclosed in many patent publications. In these patent publications, there is a description that the compound having a heterocyclic group in its molecule shows an insecticidal activity. However, according to investigations by the present inventors, it has been elucidated that every compound having a heterocyclic group does not show insecticidal activity. That is to say, among these insecticidal compounds, the compounds having the practical activity are limited to derivatives having a thiazolylmethyl group or a pyridylmethyl group. Furthermore, the compounds which are practical as insecticides are only derivatives having the pyridylmethyl group, and there is not any detailed description about a compound having a tetrahydrofuryl group such as the compound of the present invention.

The derivatives represented by the formula (1) of the present invention have a strong insecticidal function, and therefore they can be used as insecticides in various fields of agriculture, horticulture, stock raising, forestry, the prevention of epidemics, housing and the like. In addition, the derivatives represented by the formula (1) of the present invention are not harmful to plants, higher animals, environments and the like, and thus they can exert a sure prevention effect to harmful insects.

Examples of the such harmful insects include:

LEPIDOPTERA

*Pseudaletia separata* Walker—ice armyworm
*Sesamia inferens* Walker—pink borer
*Naranga aenescens* Moore—green rice caterpillar
*Agrotis ipsilon* Hufnagel—black cutworm
*Anomis flava* Fabricius—cotton leaf caterpillar
*Helicoverpa armigera* Hübner—corn earworm
*Spodoptera exigua* Hübner—beet armyworm
*Spodoptera litura* Fabricius—Common cutworm
*Agrotis segetum* Denis et Schiffermüller—cutworm
*Mamestra brassicae* Linnaeus—cabbage armyworm
*Autographa nigrisigna* Walker—beet semi-looper
*Chilo suppressalis* Walker—rice stem borer
*Cnaphalocrocis medinalis* Guenée—rice leafroller
*Scirpophaga incertulas* Walker—yellow rice borer
*Ectomyelois pyrivorella* Matsumura—pear fruit moth
*Hellulla undalis* Fabricius—cabbage webworm
*Maruca testulalis* Hübner—bean pod borer
*Parnara guttata* Bremer et Grey—rice skipper
*Pectinophora gossypiella* Saunders—pink bollworm
*Phthorimaea operculella* Zeller—potato tuberworm
*Pieris rapae crucivora* Boisduval—common cabbage worm
*Plodia interpunctella* Hübner—Indian meal worm Adoxophyes sp.
*Phyllonorycter ringoniella* Matsumura—apple leafminer
*Phyllocnistis citrella* Stainton—citrus leafminer
*Eupoecillia ambiguella* Hubner—grape cochylid
*Grapholita molesta* Busck—oriental fruit moth
*Leguminivora glycinivorella* Matsumura—soybean pod borer
*Carposina niponensis* Walsingham—peach fruit moth
*Paranthrene regalis* Butler—grape clearwing moth
*Caloptilia theivora* Walsingham—tea leafroller
*Plutella xylostella* Linnaeus—diamondback moth
*Tinea translucens* Meyrick—casemaking clothes moth

HEMIPTERA

*Bemisia tabaci* Gennadius—sweetpotato whitefly
*Trialeurodes vaporariorum* WestWood—greenhouse whitefly
*Aleurocanthus Spiniferus* Quaintance—citrus spiny whitefly
*Aphis gossypii* Glover—cotton aphid
*Aphis citricola* van der Goot—apple aphid
*Eriosoma lanigerum* Hausmann—woolly apple aphid
*Myzus persicae* Sulzer—green peach aphid
*Brevicoryne brassicae* Linnaeus—cabbage aphid
*Lipaphis erysimi* Kaltenbach—turnip aphid
*Aphis craccivora* Koch—cowpea aphid
*Toxoptera aurantii* Boyer de Fonscolumbe—black citrus aphid
*Toxoptera citricidus* Kirkaldy—tropical citrus aphid
*Viteus vitifolii* Fitch—grapeleaf louse
*Schizaphis graminum* Rondani—greenbug
*Aulacorthum solani* Kaltenbach—foxglove aphid
*Empoasca onukii* Matsuda—tea green leafhopper
*Arboridia apicalis* Nawa—grape leafhopper
*Laodelphax striatellus* Fallén—small brown planthopper
*Nilaparvata lugens* Stål—brown rice hopper
*Sogatella furcifera* Horváth—whitebacked rice planthopper
*Nephotettix cincticeps* Uhler—green rice leafhopper
*Nephotettix virescens* Distant—green rice leafhopper
*Cofana spectra* Distant—rice leafhopper
*Ceroplastes rubens* Maskell—red wax scale
*Saissetia oleae* Bernard—black scale
*Comstockaspis perniciosa* Comstock—San Jose scale
*Lepidosaphes ulmi* Linnaeus—oystershell scale
*Aonidiella aurantii* Maskell—California red scale
*Chrysomphalus ficus* Ashmead—Florida red scale
*Unaspis yanonensis* Kuwana—arrowhead scale
*Pseudococcus comstocki* Kuwana—Comstock mealybug
*Planococcus citri* Risso—citrus mealybug
*Icery purchasi* Maskell—cottonycushion scale
*Psylla mali* Schmidberger—apple sucker
*Diaphorina citri* Kuwayama—citrus psylla
*Nezara viridula* Linnaeus—southern green stink bug
*Riptortus clavatus* Thunberg—bean bug
*Stephanitis nashi* Esaki et Takeya—pear lace bug

COLEOPTERA

*Lissorhoptrus oryzophilus* Kuschel—rice water weevil
*Oulema oryzae* Kuwayama—rice leaf beetle
*Phyllotreta striolata* Fabricius—striped flea beetle
*Leptinotarsa decemlineata* Say—Colorado potato beetle
*Chaetocnema concinna* Marshall
*Diabrotica spp*
*Sitophilus zeamais* Motschulsky—maize weevil
*Carpophilus hemipterus* Linnaeus—driedfruit beetle
*Epilachna vigintioctopunctata* Fabricius—twenty-eight-spotted ladybird
*Acanthoscelides obtectus* Say—bean weevil

*Callosobruchus chinensis* Linnaeus—adzuki bean weevil
*Callosobruchus maculatus* Fabricius—cowpea weevil
*Anomala cuprea* Hope—cupreous chafer
*Anomala rufocuprea* Motschulsky—soybean beetle
*Popilla japonica* Newman—japanese beetle
*Anoplophora malasiaca* Thomson—whitespotted longicorn beetle
*Lasioderma serricorne* Fabicius—cigarette beetle
*Anthrenus verbasci* Linnaeus—varied carpet beetle
*Tribolium castaneum* Herbst—red flour beetle
*Lyctus brunneus* Stephens—powderpost beetle

HYMENOPTERA

*Culex pipiens* pallens
*Culex pipiens molestus*
*Anopheles sinensis*
*Aedes albopictus*
*Agromyza oryzae* Munakata—rice leafminer
*Asphondylia sp.*—soybean pod gall midge
*Chlorops oryzae* Matsumura—rice stem maggot
*Hydrellia griseola* Fallén—rice leafminer
*Musca domestica*—house fly
*Delia antigua* Meigen—onion maggot
*Dacus (Zeugodacus) cucurbitae* Coquillett—melon fly
*Dacus (Bactocera) dorsalis* Hendel—oriental fruit fly

THYSANOPTERA

*Thrips tabaci* Lindeman—onion thrips
*Ponticulothrips diospyrosi* Haga et Okajima
*Thrips palmi* Karny
*Stenchaetothrips biformis* Bagnall—rice thrips
*Scirtothrips dorsalis* Hood—yellow tea thrips

ORTHOPTERA

*Periplaneta fuliginosa* Servile
*Periplaneta japonica* Karny
*Periplaneta americana* Linne—American cockroach
*Blattella germanica* Linne
*Oxya yezoensis* Shiraki—rice grasshopper
*Locusta migratoria* Linnaeus—Asiatic locust

HYMENOPTERA

*Athalia rosae ruficornis* Jakovlev—cabbage sawfly

ACARINA

*Tetranychus urticae* Koch—two-spotted spider mite
*Tetranychus kanzawai* Kishida—Kanzawa spider mite
*Panonychus ulmi* Koch—European red mite
*Polyphagotarsonemus latus* Branks—broad mite
*Aculops pelekassi* Keifer—pink citrus rust mite
*Eriophyes chibaensis* Kadono
*Ornithonyssus bacoti* Hirst

TROMBICULIDAE

*Ctenocephalides canis*—dog flea
*Pediculus humanus humanus* De Geer
*Reticulitermes speratus* Kolbe
*Oxidus gracilis* C.L.Koch, and
*Thereuronema hilgendorfi* Verhoeff Two or more kinds of compounds represented by the formula (1) of the present invention an be blended to express a more excellent insecticidal activity. In addition, the compound of the formula (1) can be mixed with another physiologically active substance, whereby a multipurpose composition having an excellent efficacy can be prepared and a synergistic effect an also be expected.

Examples of the physiologically active substance include synthetic pyrethroid insecticides, their isomers and pyrethrum extracts such as allethrin, tetramethrin, resmethrin, phenothrin, furamethrin, permethrin, cypermethrin, deltamethrin, cyhalothrin, cyfluthrin, fenpropathrin, tralomethrin, cycloprothrin, flucythrinate, fluvalinate, acrinathrin, tefluthrin, bifenthrin, empenthrin, beta-cyfluthrin and zeta-cypermethrin; organic phosphorous insecticides such as DDVp, cyanophos, fenthion, fenitrothion, tetrachlorvinphos, dimethylvinphos, propaphos, methyparthion, temephos, phoxim, acephate, isofenphos, salithion, DEP, EPN, ethion, mecarbam, pyridafenthion, diazinon, pirimiphos-methyl, etrimfos, isoxathion, quinalphos, choropyriphos-methyl, chloropyriphos, phosalone, phosmet, ethidation, oxydeprofos, vamidothion, malathion, phenthoate, dimethoate, formothion, thiometon, ethylthiometon, phorate, terbufos, profenophos, prohiofos, sulprofos, pyraclofos, monocrotophos, naled and fosthiazate; carbamate insecticides such as NAC, MTMC, MIPC, BPMC, XMC, PHC, MPMC, ethiofencarb, bendiocarb, primicarb, carbosurfan, benfuracarb, methomyl,oxamyl and aldicarb; aryl propyl ether insecticides such as etofenprox and halfenprox; a silyl ether compound such as silafluofen; insecticidal natural substances suc as nicotine-sulfate, polynactin composites, avermectin, ilbemectin and BT agents; insecticides such as cartap, thiocyclam, bensultap, diflubenzuron, chlorfluazuon, teflubenzuron, triflumuron, fluofenoxuron, flucycloxuron, hexaflumuron, fluazuron, imidacloprid, nitenpyram, cetamiprid, pymetrozine, fipronil, buprofezin, fenoxycarb, pyriproxyfen, methoprene, hydroprene, kinoprene, endosulfan, diafenthiuron, triazuron, tebufenozide and benzoepin; acaricides such as dicofol, chlorobenzilate, phenisobromolate, tetradifon, CPCBS, BPPS, quinomethionate, amitraz, benzomate, hexythiazox, fenbutatin oxide, cyhexatin, dienochlor, clofentezine, pyridaben, fenpyroximate, fenazaquin tebufenpyrad and pyrimidinamine; other insecticides, acaricides, fungicides, nematocides, herbicides,plant regulators, fertilizers, soil improving materials, BT agents, microorganisms-derived toxins, natural or synthetic insect hormone disturbing agents, attractants, repellents, insect pathogenic microorganisms, small animals and other agricultural chemicals.

When the compound represented by the formula (1) of the present invention is actually applied, it can be used in a single form without adding another component, but it is usually blended with a carrier i order to facilitate its handling as the prevention agent.

For the formulation of the compound of the present invention, any particular condition are not required. In accordance with the well known procedures of usual agricultural chemicals, the compound of the present invention can be formulated into optional forms such as an emulsion, a wettable powder, a powder, grains, granules, a flowable agent, microcapsules, an oil, an aerosol, a smoking agent and a stomach poison, and they can be formulated for each use in compliance with the intended purpose.

The above-mentioned carrier means a liquid, solid or gaseous, synthetic or natural, inorganic or organic substance which can be blended with the compound of the present invention in order to aid the approach of the effective component to a site to be treated, and to facilitate the storage, transport and handling of the effective component.

Examples of the suitable solid carrier include inorganic substances such as montmorillonite, kaolinite, diatomaceous earth, terra abla, talc, vermiculite, gypsum, calcium carbonate, silica gel and ammonium sulfate, and organic substances such as soybean powder, sawdust, wheat flour, pectin, methyl cellulose, sodium alginate, vaseline, lanolin, liquid paraffin, lard and vegetable oil.

Examples of the suitable liquid carrier include aromatic hydrocarbons such as toluene, xylene, cumene and solvent naphtha, paraffin hydrocarbons such as kerosine and a mineral oil, ketones such as acetone, methyl ethyl ketone and cyclohexanone, ethers such as dioxane, tetrahydrofuran, ethylene glycol monomethyl ether, ethylene glycol dimethyl ether, diethylene glycol monomethyl ether and propylene glycol monomethyl ether, esters such as ethyl acetate, butyl acetate and glycerin esters of fatty acids, nitriles such as acetonitrile and propionitrile, alcohols such as methanol, ethanol, n-propanol, isopropanol and ethylene glycol, dimethylformamide, dimethyl sulfoxide and water.

In order to increase the effect of the compound represented by the formula (1) of the present invention, an auxiliary may be used separately or in combination therewith in consideration of the morphology of the formulation and the situation of the application in compliance with the intended purpose.

Examples of the auxiliary which can be used for the purpose of emulsification, dispersion, developing, wetting, bonding or stabilization include a water-soluble base such as lignin sulfonate, nonionic surface active agents such as alkylbenzene sulfates, alkyl sulfonates, polyoxyethylene alkylaryl ethers, polyvalent alcohol esters, lubricants such as calcium stearate and waxes, a stabilizer such as isopropylhydrodiene phosphate, methyl cellulose, carboxylmethyl cellulose, casein and gum arabic. However, these examples are not restrictive.

The compound represented by the formula (1) of the present invention is stable to light, heat and oxidation, but if necessary, an antioxidant or an ultraviolet light absorber can be added thereto as a stabilizer in a suitable amount. Examples of the antioxidant and the ultraviolet light absorber include phenol derivatives such as BHT (2,6-di-t-butyl-4-methylphenol) and BHA (butylhydroxyanisole), bisphenol derivatives, arylamines such as phenyl-α-naphthylamine, phenyl-β-naphthylamine and a condensate of phenetidine and acetone, and benzophenone compounds.

In an insecticide comprising the compound represented by the formula (1) of the present invention, this compound is contained in an amount of 0.0000001 to 95% by weight, preferably 0.0001 to 50% by weight, In applying the insecticide of he present invention, the concentration of an effective component is usually in the range of 0.001 to 5000 ppm, preferably 0.01 to 1000 ppm. In addition, the amount of the insecticide to be applied is usually in the range of 1 to 300 g per 10 a. in terms of the effective component.

Next, the present invention will be described in detail with reference to examples and reference examples. However, the scope of the present invention should not be limited to these examples at all.

EXAMPLE 1

Preparation of 1-[(tetrahydro3-furanyl)methyl]-2-(nitroimino)hexahydropyrimidine
(Compound No. 1)

A mixture of 3.72 g of (tetrahydro-3-furanyl)methyl tosylate, 15 ml of 1,3-diaminopropane 4.01 g of potassium carbonate, anhydrous, 0.1 g of sodium iodide and 80 ml of acetonitrile was stirred at 70° C. for 4 hours. After the completion of reaction, ethyl acetate was added, and insolubles were then removed by filtration. The resultant filtrate was concentrated under a reduced pressure to obtain 2.93 g of a yellow oily substance.

The thus obtained crude oily substance was mixed with 4.90 g of S-methyl-N-phthaloyl-N'-nitroisothiourea, 0.1 g of dimethylaminopyridine (DMAP) and 20 ml of ethanol, and refluxed. After the completion of reaction, ethyl acetate was added, and insolubles were then removed by filtration. The filtrate was concentrated under a reduced pressure to precipitate crystals, and the thus precipitated crystals were then removed by filtration. The filtrate was concentrated under a reduced pressure to obtain an oily substance, and this oily substance was then purified by silica gel column chromatography (1:2 acetone/ethyl acetate) to obtain 2.32 g of 1-[(tetrahydro-3-furanyl) methyl]-2-(nitroimino)hexahydropyrimidine as a pale yellow oil.

Melting point: 87.5°–90.8° C.

$^1$HNMR (CDCl$_3$, ppm): 1.56–1.72 (1H, m), 1.96–2.12 (3H, m), 2.67–2.82 (1H, m), 3.32–3.57 (5H, m), 3.62–3.95 (5H, m), 9.79 (1H, br-s).

IR (KBr, cm$^{-1}$): 3256, 1593, 1321, 1243, 1156.

EXAMPLE 2

Preparation of 1-[(2-methyl-4-tetrahydrofuryl) methyl]-2-(nitroimino)hexahydropyrimidine
(Compound No. 2)

To a solution of 1.37 g of S-methyl-N-nitro-N'phthaloylisothiourea in 15 ml of dichloromethane was added a solution of 0.89 g of N-[(2-methyl4-tetrahydrofuryl)methyl]-1,3-diaminopropane in 5 ml of dichloromethane under ice-cooling, and the mixture was then stirred under ice-cooling for 1 hour and at room temperature for 30 minutes, followed by refluxing for 2 hours. After cooling to room temperature, insolubles were then removed by filtration. The filtrate was concentrated under a reduced pressure to obtain an oily substance, and this oily substance was then purified by silica gel column chromatography (ethyl acetate). In consequence, 0.58 g of 1-[(2-methyl-4-tetrahydrofuryl)methyl]-2-(nitroimino) hexahydropyrimidine was obtained a$_s$ a colorless oil.

$^1$HNMR (CDCl$_3$, ppm): 1.21–1.29 (3H, m), 1.55–1.86 (2H, m), 2.01–2.15 (2H, m), 2.69–2.86 (1H, m), 3.32–3.50 (5H, m), 3.57–3.84 (2H, m), 3.92–4.00 (1H, m), 4.08–4.18 (1H, m), 9.78 (1H, br-s).

IR (neat, cm$^{-1}$): 3275, 2969, 2931, 2870, 1734, 1716, 1592, 1560, 1423, 1321, 1241, 1163, 1119, 1020, 896, 781, 713.

EXAMPLE 3

Preparation of 1-[(2,2-dimethyl+4-tetrahydrofuryl) methyl]-2-(nitroimino)hexahydropyrimidine
(Compound No. 3)

To a solution of 5.00 g of (2,2dimethyl-4-tetrahydrofuran)-methanol and 4.08 g of triethylamine in 25 ml of tetrahydrofuran was dropwise added a solution of 4.62 g of methanesulfonyl chroride in 10 ml of tetrahydrofuran over 30 minutes under ice-cooling, and the mixture was then stirred for 2 hours under ice-cooling. Insolubles formed by reaction were removed by filtration, and the filtrate was then concentrated under a reduced pressure to obtain crude [(2,2-dimethyl-4-tetrahydrofuryl)methyl] methanesuloate as an oil. Next, to this crude oil was added a suspension of 14.2 g of 1,2-diaminopropane and 10.6 g of potassium carbonate in 50 ml of acetonitrile, and the mixture was then stirred for 2 hours at 60° C. The mixture was cooled to room temperature, and insolubles were then removed. Afterward, 1,2- diaminopropane and acetonitrile were distilled off, and 100 ml of a 2N aqueous solution of sodium hydroxide was then added thereto, followed by extraction with dichloromethane, The organic layer was dried over magnesium sulfate, anhydrous, and then concentrated under reduced a pressure to obtain crude N-[(2,2-dimethyl-4-tetrahydrofuryl) methyl]-1,2-diaminopropane as a pale yellow oil. Next, this crude oil was dissolved in 10 ml of dichloromethane, and then the mixture was dropwise added to a solution of 8.15 g of S-methyl-N-nitro-N'-phthaloylisothiourea in 30 ml of dichloromethane over 30 minutes under ice-cooling. After stirring under ice-cooling for 1 hour, the reaction solution was refluxed for 2 hours. After cooling to room temperature, insolubles were then removed by filtration. The filtrate was concentrated under a reduced pressure to obtain an oily substance, and this oily substance was purified by silica gel column chromatography (ethyl acetate) to afford crystals. Afterward, the crystals were washed with diethyl ether to obtain 1.60 g of 1-[(2,2-dimethyl-4-tetrahydrofuryl)methyl]-2-(nitroimino)hexahydropyrimidine as colorless crystals.

Melting point: 109.3°–110.1° C.

$^1$HNMR (CDCl$_3$, ppm): 1.21 (3H, s), 1.31 (3H, s), 2.60–2.70 (1H, m), 3.26–3.51 (2H, m), 3.61–3.68 (2H, m), 3.77–3.83 (2H, m), 3.92–4.15 (2H, m), 8.13 (1H, br-s).

IR (KBr, cm$^{-1}$): 3392, 2969, 2928, 2869, 1554, 1456, 1379, 1271, 1218, 1104, 1044, 974, 957, 919, 814, 784, 747, 719.

EXAMPLE 4

Preparation of
1-[(tetrahydro-3-furanyl)methyl]-2-(nitroimino)imidazolidine (Compound No. 4)

A mixture of 4.74 g of tetrahydro-3-furanyl tosylate, 15 ml of ethylenediamine, 5.11 g of potassium carbonate, anhydrous, and 0.1 g of sodium iodide was stirred for 4 hours at 60° C. After the completion of reaction, ethyl acetate was added, and insolubles were then removed by filtration. The filtrate was concentrated under a reduced pressure to obtain 4.00 g of a yellow oily substance as a desired product.

The thus obtained crude oily substance was mixed with 3.07 g of S-methyl-N-nitroisothiourea, 0.1 g of dimethylaminopyridine (DMAP) and 30 ml of ethanol, and the mixture was refluxed. After the completion of reaction, ethyl acetate was added, and insolubles were then removed by filtration. The filtrate was concentrated under a reduced pressure to precipitate crystals, and the thus precipitated crystals were then removed by filtration. Next, the filtrate was concentrated under a reduced pressure to obtain an oily substance, and this oily substance was then purified by silica gel column chromatography (1:2 acetone/ethyl acetate) to obtain 1.04 g of 1-[(tetrahydro-3-furanyl)methyl]-2-(nitroimino)imidazolidine as a pale yellow oil.

Refractive index: nD (19.9° C.)=1.4470.

$^1$HNMR (CDCl$_3$, ppm): 1.58–1.71 (1H, m), 1.99–2.09 (1H, m), 2.60 (1H, septet, J=7.3 Hz), 3.33 (1H, dd, J=7.3 Hz, J=14.0 Hz), 3.44 (1H, dd, J=7.3 Hz, J=14.0 Hz), 3.51 (1H, dd, J=5.9 Hz, J=8.8 Hz), 3.62–3.94 (7H, m), 8.15 (1H, br-s).

IR (neat, cm$^{-1}$): 3412, 1619, 1545, 1451, 1283.

EXAMPLE 5

Preparation of 1-[(2-methyl-4-tetrahydrofuryl)methyl]-2-(nitroimino)imidazolidine
(Compound No. 5)

To a solution of 1.76 g of S-methyl-N-nitro-N'-phthaloylisothiourea in 10 ml of dichloromethane was added a solution of 0.70 g of N-[(2-methyl-4-tetrahydrofuryl) methyl]-1,2-diaminoethane in 5 ml of dichloromethane under ice-cooling, and the mixture was then stirred under ice-cooling for 1 hour and at room temperature for 30 minutes, followed by refluxing for 2 hours. After cooling to room temperature, insolubles were then removed by filtration. The filtrate was concentrated under a reduced pressure to obtain an oily substance, and this oily substance was then purified by silica gel column chromatography (ethyl acetate), and then recrystallized (ethyl acetate-hexane) to obtain 108 mg of 1-[(2-methyl-4-tetrahydrofuryl)methyl]-2-(nitroimino)imidazolidine as colorless crystals.

Melting point: 109.3°–110.1° C.

$^1$HNMR (CDCl$_3$, ppm): 1.22–1.29 (3H, m), 1.57–1.85 (3H, m), 2.60–2.70 (1H, m), 3.26–3.51 (2H, m), 3.61–3.68 (2H, m ), 3.77–3.83 (2H, m), 3.92–4.15 (2H, m), 8.13 (1H, br-s).

IR (KBr, cm$^{-1}$): 3392, 2969, 2928, 2869, 1554, 1456, 1379, 1271, 1218, 1104, 1044, 974, 957, 919, 814, 784, 747, 719.

EXAMPLE 6

Preparation of 1-[(2,2-dimethyl-4-tetrahydrofuryl)methyl]-2-(nitroimino)imidazolidine
(Compound No. 6)

(1) Synthesis of [(2,2-dimethyl-4-tetrahydrofuryl)methyl] methanesulfonate

To a solution of 5.00 g of (2,2-dimethyl-4-tetrahydrofuran) methanol and 3.97 g of triethylamine in 10 ml of tetrahydrofuran was added a solution 4.40 g of methanesulfonyl chloride in 10 ml of tetrahydrofuran under ice-cooling, and the mixture was then stirred under ice-cooling for 30 minutes and at room temperature for 2 hour. Insolubles formed by reaction were removed by filtration, and the filtrate was then concentrated under a reduced pressure. The resultant oily substance was purified by silica gel column chromatography (1:1 hexane/ethyl acetate), thereby obtaining 6.01 g of [(2,2-dimethyl-4-tetrahydrofuryl) methyl] methanesulfonate as a colorless oil.

(2) Synthesis of N-[(2,2-dimethyl-4-tetrahydrofuryl) methyl]-1,2-diaminoethane

A suspension of 4.00 g of [(2,2-dimethyl-4-tetrahydrofuryl) methyl]methanesulfonate, 10.4 g of 1,2-diaminoethane and 2.87 g of potassium carbonate in 40 ml of acetonitrile was stirred at 80° C. for 3 hours. The mixture was cooled to room temperature, and water was then added thereto, followed by extraction with dichloromethane, The organic layer was dried over magnesium sulfate, anhydrous, and then concentrated under a reduced pressure to obtain 1.38 g of N-[(2,2-dimethyl-4-tetrahydrofuryl) methyl]-1,2-diaminoethane as a pale yellow oil.

(3) Synthesis of 1-[(2,2-dimethyl-4-tetrahydrofuryl)methyl]-2-(nitroimino)imidazolidine To a solution of 1.05 g of S-methyl-N-nitro-N'-phthaloylisothiourea in 10 ml of dicloromethane was dropwise added a solution of 0.68 g of N-[(2,2-dimethyl-4-tetrahydrofuryl)-methyl]-1,2-diaminoethane in 5 ml of dichloromethane under ice-cooling over 30 minutes. After stirring under ice-cooling for 1 hour, the mixture was refluxed for 2 hours. Next, the mixture was cooled to room temperature, and insolubles were then removed by filtration. The filtrate was concentrated under a reduced pressure, and the resultant oily substance was purified by silica gel column chromatography (ethyl acetate), and then recrystallized (ethyl acetate-diethyl ether) to obtain 0.24 g of 1-[(2,2-dimethyl-4-tetrahydrofuryl)methyl]-2-(nitroimino)imidazolidine as colorless crystals.

Melting point: 118.8°–119.8° C.

$^1$HNMR (CDCl$_3$, ppm): 1.21 (3H, s), 1.31 (3H, s), 1.46 (1H, dd, J=12.5), 1.93 (1H, dd, J=12.5), 2.70 (1H, septet, J=8.1), 3.31–3.49 (2H, m), 3.53–3.71 (3H, m), 3.77–3.84 (2H, m), 3.94–4.00 (1H, m), 8.12 (1H, br).

IR (KBr, cm$^{-1}$): 3414, 2972, 1553, 1452, 1269, 1221, 1041.

MH+: 243.

EXAMPLE 7

Preparation of 1-(methylcarbonyl)-2-(nitroimino)-3-[(tetrahydro-3-furanyl)methyl]imidazolidine (Compound No. 7)

0.09 g of acetyl chloride was added to a mixture of 0.20 g of 1-(tetrahydro-3-furanyl)methyl-2-(nitroimino)imidazolidine, 0.05 g of sodium hydride (60%) and 10 ml of dimethylformamide (DMF), followed by stirring at 40° C. for 2 hours.

After the completion of reaction, the mixture was poured into 20 ml of water, followed by extraction with methylene chloride twice. The organic layer was dried over sodium sulfate, anhydrous, and then concentrated under a reduced pressure. The resultant oily substance was purified by silica gel column chromatography (2:1 ethyl acetate/acetone) to obtain 0.19 g of 1-(methylcarbonyl)-2-(nitroimino)-3-[(tetrahydro-3-furanyl) methyl]imidazolidine as an oil.

$^1$HNMR (CDCl$_3$, ppm): 1.57–1.73 (1H, m), 2.02–2.15 (1H, m), 2.40 (3H, s), 2.54–2.72 (1H, m), 3.27–3.54 (3H, m), 3.58–3.97 (5H, m), 4.00–4.18 (2H, m).

IR (neat, cm$^{-1}$): 2934, 1718, 1490, 1256.

EXAMPLE 8

Preparation of 1-(methylcarbonyl)-2-(nitroimino)-3-[(tetrahydro-3-furanyl)methyl]hexahydropyrimidine (Compound No. 8)

A mixture of 0.30 g of 1-[(tetrahydro-3-furanyl) methyl] -2-(nitroimino)hexahydropyrimidine, 0.07 g of sodium hydride (60%) and 10 ml of acetonitrile was stirred at 50° C. for 30 minutes. After this mixture was cooled on ice, 0.11 g of acetyl chloride was dropwise added thereto over 10 minutes, and the mixture was then stirred at room temperature for 2 hours. After the completion of reaction, insolubles were removed by filtration, and concentration was then carried out under a reduced pressure. The resultant oily substance was purified by silica gel column chromatography (2:1 ethyl acetate/acetone) to obtain 0.06 g of 1-(methylcarbonyl)-2-(nitroimino)-3-[(tetrahydro-3-furanyl)methyl] hexahydropyrimidine.

Oily substance.

$^1$HNMR (CDCl$_3$, ppm): 1.57–1.77 (1H, m), 1.99–2.28 (3H, m), 2.32 (3H, s), 2.63–2.85 (1H, m), 3.41–3.62 (4H, m), 3.67–3.98 (6H, m).

IR (neat, cm$^{-1}$): 2939, 17016, 1569, 1238.

EXAMPLE 9

Preparation of 1-(isopropylcarbonyl)-2-(nitroimino)-3-[(tetrahydro-3-furanyl)methyl]hexahydropyrimidine (Compound No. 9)

A mixture of 2.2 g of 1-[(tetrahydro-3-furanyl) methyl]-2-(nitroimino)hexahydropyrimidine, 0.58 g of sodium hydride (60%) and 100 ml of acetonitrile was stirred at 50° C. for 30 minutes. After this mixture was cooled on ice, 1.58 g of isobutanoyl chloride was added dropwise thereto over 30 minutes, an$_d$ the mixture was then stirred at room temperature for 2 hours. After the completion of reaction, insolubles were removed by filtration, and concentration was then carried out under a reduced pressure. The resultant residue was purified by silica gel column chromatography (2:1 ethyl acetate/acetone) to obtain 1.30 g of 1-(isopropylcarbonyl)-2-(nitroimino)-3-[(tetrahydro-3-furanyl)methyl] hexahydropyrimidine Oily substance.

$^1$HNMR (CDCl$_3$, ppm): 1.12 (6H, d, J=6.6), 1.57–1.80 (1H, m), 1.98–2.20 (1H, m), 2.19 (2H, quint., J=6.6), 2.67–2.88 (1H, m), 3.16 (1H, septet, J=6.6), 3.37–3.61 (4H, m), 3.66–4.00 (6H, m).

IR (neat, cm$^{-1}$): 2975, 1706, 1566, 1490, 1237.

EXAMPLE 10

Preparation of 1-(methylcarbonyl)-3-[(2-methyl-4-tetrahydrofuryl) methyl]-2-(nitroimino) hexahydropyrimidine (Compound No. 10)

To a suspension of 0.20 g of sodium hydride (60%, oily) in 30 ml of acetonitrile was added a solution of 1.00 g of 1-[(2-methyl-4-tetrahydrofuryl)methyl]-2-(nitroimino) hexahydropyrimidine in 5 ml of acetonitrile at room temperature, followed by stirring for 30 minutes. Next, to the mixture was added a solution of 0.39 g of acetyl chloride in 5 ml of acetonitrile under ice-cooling, and the mixture was then stirred under ice-cooling for 30 minutes and at room temperature for 3 hours. Afterward, insolubles were removed by filtration, and the filtrate was then concentrated under a reduced pressure. The resultant oily substance was purified by silica gel column chromatography (20:1 chloroform/methanol) to obtain 1.15 g of 1-(methylcarbonyl)-3-[(2-methyl-4-tetrahydrofuryl) methyl]-2-(nitroimino-)hexahydropyrimidine as a yellow oil.

$^1$HNMR (CDCl$_3$, ppm): 1.21–1.30 (3H, m), 1.79–2.14 (1H, m), 2.16–2.23 (2H, m), 2.32 (3H, s), 2.70–2.82 (1H, m), 3.43–4.18 (10H, m).

IR (neat, cm$^{-1}$): 3275, 2970, 2935, 2871, 1708, 1568, 1489, 1372, 1293, 1235, 1102, 1033, 993.

EXAMPLE 11

Preparation of 1-(ethylcarbonyl)-2-(nitroimino)-3-[(tetrahydro-3-furanyl)methyl]hexahydopyrimidine (Compound No. 11)

A mixture of 0.33 g of 1-[(tetrahydro-3-furanyl) methyl] -2-(nitroimino)hexahydropyrimidine, 0.07 g of sodium hydride (60%) and 10 ml of acetonitrile was stirred at 50° C. for 30 minutes. After this mixture was cooled on ice, 0.16 g of propionyl chloride was added dropwise thereto over 30 minutes, and the mixture was then stirred at room temperature for 2 hours. After the completion of reaction, insolubles were removed by filtration, and the filtrate was then concentrated under a reduced pressure. The resultant residue was purified by silica gel column chromatography (2:1 ethyl acetate/acetone) to obtain 0.08 g of 1-(ethylcarbonyl)-2-(nitroimino)-3-[(tetrahydro-3-furanyl)methyl]hexahydropyrimidine.

Oily substance.

$^1$HNMR (CDCl$_3$, ppm): 1.15 (3H, t, J=7.3), 1.52–1.78 (1H, m), 1.98–2.19 (1H, m), 2.19 (2H quint., J=6.6), 2.60 (2H, q, J=7.3), 2.61–2.83 (1H, m), 3.33–3.62 (4H, m), 3.65–4.00 (6H, m).

IR (neat, cm$^{-1}$): 2939, 1706, 1568, 1456, 1235.

EXAMPLE 12

Preparation of 1-(propylcarbonyl)-2-(nitroimino)-3-[(tetrahydro-3-furanyl)methyl]imidazolidine (Compound No. 12)

A mixture of 0.30 g of 1-[(tetrahydro-3-furanyl)methyl]-2-(nitroimino)imidazolidine, 0.084 g of sodium hydride (60%) and 10 ml of acetonitrile was stirred at 50° C. for 30 minutes. After this mixture was cooled on ice, 0.22 g of n-butanoyl chloride was added dropwise thereto over 30 minutes, and the solution was then stirred at room temperature for 2 hours. After the completion of reaction, insolubles were removed by filtration, and the filtrate was then concentrated under a reduced pressure. The resultant residue was purified by silica gel column chromatography (2:1 ethyl acetate/acetone) to obtain 0.27 g of 1-(propylcarbonyl)-2-(nitroimino)-3-[(tetrahydro-3-furanyl) methyl]imidazolidine.

Oily substance.

$^1$HNMR (CDCl$_3$, ppm): 0.96 (3H, t, J=7.3), 1.57–1.82 (3H, m), 1.95–2.23 (1H, m), 2.50–2.73 (3H, m), 3.25–4.20 (10H, m).

IR (neat, cm$^{-1}$): 2971, 1718, 1560,1258.

EXAMPLE 13

Preparation of 1-propionyl-2-(nitroimino)-3-[(tetrahydro-3-furanyl)methyl]hexahydropyrimidine (Compound No. 13)

A mixture of 3.0 g of 1-[(tetrahydro-3-furanyl)methyl]-2-(nitroimino)hexahydropyrimidine, 0.70 g of sodium hydride (60%) and 100 ml of acetonitrile was stirred at 50° C. for 30 minutes. After this mixture was cooled on ice, 1.60 g of propionyl chloride was added dropwise thereto over 30 minutes, and the solution was then stirred at room temperature for 2 hours. After the completion of reaction, insolubles were removed by filtration, and the filtrate was then concentrated under a reduced pressure. The resultant residue was purified by silica gel column chromatography (2:1 ethyl acetate/acetone) to obtain 0.80 g of 1-propionyl-2-(nitroimino)-3-[(tetrahydro-3-furanyl)methyl]hexahydropyrimidine.

Oily substance.

$^1$HNMR (CDCl$_3$, ppm): 1.26 (3H, t, J=6.6), 1.58–1.78 (3H, m), 2.00–2.26 (3H, m), 2.55 (2H, t, J=7.3), 2.63–2.85 (1H, m), 3.41–3.62 (4H, m), 3.67–3.97 (6H, m).

IR (neat, cm$^{-1}$): 2970, 2875, 1709, 1567, 1236, 1049.

Example 14

Preparation of 1-[(tetrahydro-3-furanyl)methyl]-2-(nitroimino)imidazolidine (Compound No. 4)

A mixture of 2.0 g of 1-(1-propenyl)-2-nitroimino-3-[(tetrahydro-3-furanyl)methyl]imidazolidine, 20 ml of 2N hydrochloric acid and 20 ml of ethanol was stirred at 60° C. for 3 hours. After the completion of reaction, the reaction mixture was neutralized with an aqueous solution of saturated sodium bicarbonate, followed by extraction with methylene chloride three times. Next, the extract was dried over sodium sulfate, anhydrous and then concentrated under a reduced pressure. The resultant oily substance was purified by silica gel column chromatography (ethyl acetate) to obtain 1.02 g of 1-[(tetrahydro-3furanyl)methyl]-2-(nitroimino)imidazolidine as a pale yellow oil.

REFERENCE EXAMPLE 1

Preparation of 1-[(tetrahydro-2-furanyl)methyl]-2-(nitroimino)imidazolidine
[Comparative compound (1)]

Mesyl chloride (6.17 g) was dropwise added to a solution of 5.0 g of (tetrahydro-2furanyl)methanol, 2.18 g of triethylamine and 30 ml of tetrahydrofuran under ice-cooling over 30 minutes, followed by stirring at the same temperature for 2 hours. After the completion of reaction, the insolubles were filtered, and the filtrate was then concentrated under a reduced pressure to obtain (tetrahydro-2-furanyl)methyl methanesulfonate as an oil.

A mixture of 1.42 g of (tetrahydro-2-furanyl)methyl methanesulfonate, 5 ml of ethylendiamine, 1.53 g of potassium carbonate, anhydrous, and 0.1 g of sodium iodide was stirred at 60° C. for 4 hours. After the completion of reaction, ethyl acetate was added, and insolubles were then removed by filtration. The filtrate was concentrated under a reduced pressure, and the resultant residue was poured into 10 ml of a 6N aqueous solution of sodium hydroxide, followed by extraction with 100 ml of methylene chloride. Next, the extract was dried over sodium sulfate, anhydrous, and then concentrated under a reduced pressure to obtain 1.2 g of N-[(tetrahydro-2-furanyl) methyl]ethylenediamine as a yellow oil.

Afterward, a mixture of 1.00 g Of N-[(tetrahydro-2-furanyl) methyl]ethylenediamine, 0.77/g of S-methyl-N-nitroisothiourea, 0.1 g of N,N-dimethylaminopyridine (DMAP) and 10 ml of ethanol was refluxed. After the completion of reaction, ethyl acetate was added, and insolubles were then removed by filtration. The filtrate was concentrated under a reduced pressure, and the precipitated crystals were then removed by filtration. Next, the filtrate was concentrated under a reduced pressure, and the resultant residue was purified by silica gel column chromatography (1:2 acetone/ethyl acetate) to obtain 0.25 g of 1-[(tetrahydro-2-furanyl) methyl]-2(nitroimino)imidazolidine as a pale yellow oil.

$^1$HNMR (CDCl$_3$, ppm): 1.48–1.65, (1H, m), 1.80–2.12 (3H, m), 3.17 (1H, dd, J=8.8, J=14.7), 3.62–4.18 (8H, m), 8.11 (1H, br-s).

IR (neat, cm$^{-1}$): 3409, 2877, 1562, 1449, 1289, 1068.

REFERENCE EXAMPLE 2

[(Tetrahydro-3-furanyl)methyl]bromide 10 g of (tetrahydro-3-furanyl)methanol was added dropwise to a mixture 31.8 g of phosphorus tribromide, 9.29 g of pyridine and 100 ml of ether over 30 minutes, and the mixture was then stirred for 5.5 hours. Next, the reaction mixture was concentrated under a reduced pressure, and the resultant residue was purified by silica gel column chromatography (1:1 ethyl acetate/hexane) to obtain 8.6 g of [(tetrahydro-3-furanyl)methyl]bromide.

$^1$HNMR (CDCl$_3$, ppm): 1.62–1.76 (1H, m), 2.05–2.16 (1H, m), 2.70 (1H, septet, J=7.3), 3.40 (2H, dd, J=1.5, J=7.3), 3.45–3.53 (1H, m), 3.60 (1H, dd, J=5.1, J=8.8), 3.80 (1H, t, J=7.3), 3.89–3.95 (1H, m).

REFERENCE EXAMPLE 3

[(Tetrahydro-3-furanyl)methyl]trifluoromethanesulfonate

A mixture of 2.0 g of (tetrahydro-3-furanyl)methanol, 5.9 g of trifluoromethanesulfonic anhydride, 2.0 g of pyridine and 50 ml of dichloromethane was stirred at room temperature for 1 hour. Next, water was poured into the reaction mixture, and the resultant organic layer was separated, washed with 1N hydrochloric acid, water and an aqueous solution of saturated sodium Chloride, dried, and then concentrated to obtain 4.0 g of [(tetrahydro-3-furanyl) methyl] trifluoromethanesulfonate,

REFERENCE EXAMPLE 4

[(Tetrahydro-3-furanyl)methyl]p-toluenesulfonate

A mixture of 5.0 g of (tetrahydro-3-furanyl)methanol, 10.3 g of tosyl chloride, 5.44 g of triethylamine and 50 ml of tetrahydrofuran was stirred at 70° C. for 3 hours, Since the reaction did not finish, the mixture was further stirred at 80° C. for 3 hours.

After the completion of the reaction, the reaction mixture was poured into water, extracted with the mixture of acetone and hexane (1:1). The organic layer was washed with water twice, washed with salt Water, dried over sodium sulfate, anhydrous, and then concentrated under a reduced pressure. The resultant oily substance was purified by silica gel column chromatography (1:1 ethyl acetate/hexane) to obtain 9.81 g of [(tetrahydro-3-furanyl)methyl] p-toluenesulfonate.

Next, the compositions of the present invention will be described in detail with reference to examples of formulations.

FORMULATION EXAMPLE 1

20 parts of a compound of the present invention, 10 parts of Sorpol 355S (made by Toho Chemical Co., Ltd., a surface active agent), 70 parts of xylene were uniformly stirred and mixed to obtain an emulsion. Here, the parts mean parts by weight, which will apply to the following.

FORMULATION EXAMPLE 2

10 parts of a compound of the present invention, 2 parts of sodium alkylnaphthalenesulfonate, 1 part of sodium ligninsulfonate, 5 parts of white carbon and 82 parts of diatomaceous earth were uniformly stirred and mixed to obtain 100 parts of a wettable powder.

FORMULATION EXAMPLE 3

0.3 part of a compound of the present invention and 0.3 part of white carbon were uniformly mixed, and 99.2 parts of clay and 0.2 part of Driless A (made by Sankyo Co., Ltd.) were then added thereto. Afterward, the mixture was uniformly ground and mixed to obtain 100 parts of a power.

FORMULATION EXAMPLE 4

2 parts of a compound of the present invention, 2 parts of white carbon, 2 parts of sodium ligninsulfonate and 94 parts of bentonite were uniformly ground and mixed. Afterward, water was added thereto, and the mixture was kneaded, granulated, and then dried to obtain 100 parts of grains.

FORMULATION EXAMPLE 5

20 parts of a compound of the present invention and 5 parts of a 20% aqueous polyvinyl alcohol solution were sufficiently stirred and mixed, and 75 parts of a 0.8% aqueous xanthane gum solution was then added thereto. Next, the mixture was stirred and mixed again to obtain 100 parts of a flowable agent.

FORMULATION EXAMPLE 6

10 parts of a compound of the present invention, 3 parts of carboxymethyl cellulose, 2 parts of sodium ligninsulfonate, 1 part of sodium dioctylsulfosuccinate and 84 parts of water were uniformly wet-ground to obtain 100 parts of a flowable agent.

Next, in order to elucidate that the compound represented by the formula (1) of the present invention has an excellent insecticidal activity, test examples will be described in detail.

TEST EXAMPLE 1

Effect on *Laodelphax striatellus* Fallen—Smaller brown planthopper

Each compound of the present invention was dissolved in acetone to prepare an acetone solution having a predetermined concentration, and 3 ml of the acetone solution was applied over a bundle of several rice seedlings (about third leaf stage). After drying in air, the treated seedlings were covered with a metal gauze cylinder, and ten female adults of smaller brown planthopper were introduced into the cylinder. Afterward, this cylinder was placed in a temperature controlled room at 25° C. and after 48 hours, mortality was checked. The results are shown in Table 1.

TABLE 1

| | Effect on smaller brown planthopper | |
|---|---|---|
| | Mortality (%) | |
| Compound No. | 1000 ppm | 200 ppm |
|---|---|---|
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |
| Comparative Compound (1) | 20 | 0 |
| Comparative Compound (2) | 40 | 0 |
| Untreated | 0 | 0 |

Comparative Compound (1): 1-[(tetrahydro-2-furanyl)methyl]-2-(nitroimino)imidazolidine
Comparative Compound (2): 1-[(3-furanyl)methyl]-2-(nitroimino)imidazolidine (a compound mentioned in Japanese Patent Application Laid-open No. 81382/1987)

TEST EXAMPLE 2

Effect on resistant strain of *Nepphotettix cincticeptus* Unler—Resistant green rice leafhopper Each compound of the present invention was dissolved in acetone to prepare an acetone solution having a predetermined concentration, and 3 ml of the acetone solution was applied over a bundle of several rice seedlings (about third leaf stage). After drying in air, the treated seedlings were covered with a metal gauze cylinder, and ten female adults of resistant green rice leafhopper were introduced into the cylinder. Afterward, this cylinder was placed in a temperature controlled room at 25° C., and after 48 hours, mortality was checked. The results are shown in Table 2.

TABLE 2

Effect on resistant green rice leafhopper

| Compound No. | Mortality (%) 1000 ppm | 200 ppm |
|---|---|---|
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |
| Comparative Compound (1) | 30 | 0 |
| Untreated | 0 | 0 |

Comparative Compound (1): 1-[(tetrahydro-2-furanyl)methyl]-2-(nitroimino)imidazolidine

TEST EXAMPLE 3

Effect on *Spodoptera litura* Fabricius—Common cutworm

The emulsion of each compound of the present invention prepared according to Formulation Example 1 was diluted with distilled water to a predetermined concentration, and a spreading agent New Gramin, made by Sankyo Co., Ltd.) was then added thereto so that its concentration might be 0.02%. Then, 3leaves of *Ipomea batatas* were fully immersed in the solution. After drying in air, the leaves were placed in a plastic cup having a diameter of 9 cm and a depth of 4 cm, and 10 second instar larvae of common cutworm were allowed to eat the leaves at 25° C. After 72 hours, mortality was checked. The results are shown in Table 3.

TABLE 3

Effect on common cutworm

| Compound No. | Mortality (%) 1000 ppm |
|---|---|
| 1 | 70 |
| 4 | 100 |
| 7 | 100 |
| 10 | 100 |
| 11 | 70 |
| 12 | 100 |
| 13 | 100 |
| Comparative Compound (1) | 0 |
| Comparative Compound (2) | 0 |
| Comparative Compound (3) | 0 |
| Untreated | 0 |

Comparative Compound (1): 1-[(tetrahydro-2-furanyl)methyl]-2-(nitroimino)imidazolidine
Comparative Compound (2): 1-[(3-furanyl)methyl]-2-(nitroimino)imidazolidine (a compound mentioned in Japanese Patent Application Laid-open No. 81382/1987)
Comparative Compound (3): 1-[(tetrahydro-3-furanyl)methyl]-2-(nitromethylene)hexahydropyrimidine (a compound mentioned in Japanese Patent Application Laid-open No. 183271/1986)

TEST EXAMPLE 4

Effect on *Myzus persicae* Sulzer—Green peach aphid

The emulsion of each compound of the present invention prepared according to Formulation Example 1 was diluted with distilled water to a predetermined concentration, and a spreading agent (New Gramn, made by Sankyo Co., Ltd.) was then added thereto so that its concentration might be 0.02%. Then, the thus prepared chemical solution was sprayed over eggplant seedlings of 2nd and 3rd plastochrons, on which green peach aphids had been parasitic, and the seedlings were the cultivated in a hothouse. After 48 hours, the number of the alive green peach aphid was counted to calculate mortality. The results are shown in Table 4.

TABLE 4

Effect on green peach aphid

| Compound No. | Mortality (%) 100 ppm | 10 ppm |
|---|---|---|
| 1 | 100 | 100 |
| 2 | 100 | 100 |
| 3 | 100 | 100 |
| 4 | 100 | 67 |
| 5 | 100 | 100 |
| 6 | 100 | 82 |
| 7 | 100 | 63 |
| 8 | 100 | 100 |
| 9 | 100 | 86 |
| 10 | 100 | 100 |
| 11 | 100 | 100 |
| 12 | 66 | 0 |
| 13 | 100 | 27 |
| Comparative Compound (1) | 0 | 0 |
| Untreated | 0 | 0 |

Comparative Compound (1): 1-[(tetrahydro-2-furanyl)methyl]-2-(nitroimino)imidazolidine Next, in order to clarify that the compounds represented by the formula (1) of the present invention are extremely less harmful to mammals, the following test example will be described in detail.

TEST EXAMPLE 5

Acute toxicity to mice 5-week-old male mice (Crj: CD-1) were purchased and then tamed for 1 week, and so the mice of 6 weeks old were tested. The mice were bred in a breeding chamber having a temperature of 23°±2° C., a humidity of 50±10%, a ventilation frequency of 15 times/hour and a lighting time of 12 hours/day. A solid feed (CE-2, made by Nippon Clea) was given, and as drinking water, tap water was freely given.

Each compound to be tested was Suspended in acetone:corn oil (1:9) by the use of a high-speed homogenizer, and then orally administered forcedly to the mice to be tested through a stomach tube. The amount of the solution to be administered was 0.1 ml with respect to 10 g of weight (10 ml/kg).

One administration group was constituted of 5 mice, and an observation period was 14 days from the administration. The results are shown in Table 5.

TABLE 5

| Acute toxicity to mice [survival rate (%)] | | |
|---|---|---|
| Compound | LD$_{50}$ value (mg/kg) | Note |
| No. 1 | >300 | Corresponding to common material |
| No. 2 | >500 | Corresponding to common material |
| Comparative Compound (4) | 30–100 | Corresponding to dangerous drug |

Comparative Compound (4): 1-[(2-chloropyridine-5-yl)methyl]-2-(nitroimino)hexahydropyrimidine (a compound mentioned in Japanese Patent Application Laid-open No. 267575/1986)

What is claimed is:

1. A tetrahydrofuran-compound represented by formula (1)

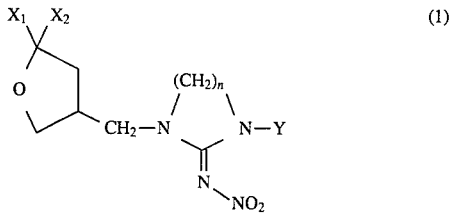

wherein each of $X_1$ and $X_2$ is a hydrogen atom or a methyl group, Y is a hydrogen atom or a carbonyl group substituted by a lower alkyl group (Y') having 1 to 4 carbon atoms, so as to form an acyl group (—COY'), and n is 3.

2. The tetrahydrofuran-compound of claim 1 wherein each of $X_1$ and $X_2$ is a hydrogen or a methyl group and Y is a hydrogen atom or a carbonyl group (—COY') substituted by a lower alkyl group (Y') having 1 to 4 carbon atoms.

3. The tetrahydrofuran-compound of claim 1 wherein each of $X_1$ and $X_2$ is a hydrogen atom and Y is a hydrogen atom.

4. The tetrahydrofuran-compound of claim 1 wherein $X_1$ is a hydrogen atom, $X_2$ is a methyl group and Y is a hydrogen atom.

5. An insecticidal composition comprising a carrier and an effective amount of a compound of claim 1.

6. The insecticide of claim 1 wherein each of $X_1$ and $X_2$ is a hydrogen atom or a methyl group and Y is a hydrogen atom or a carbonyl group (—COY') substituted by a lower alkyl group (Y') having 1 to 4 carbon atoms.

7. The insecticidal composition of claim 5 wherein each of $X_1$ and $X_2$ is a hydrogen atom and Y is a hydrogen atom.

8. The insecticidal composition of claim 5 wherein $X_1$ is a hydrogen atom, $X_2$ is a methyl group and Y is a hydrogen atom.

* * * * *